United States Patent [19]

Ho

[11] Patent Number: 5,023,323
[45] Date of Patent: Jun. 11, 1991

[54] METHOD OF SOMATOTROPIN NATURATION

[75] Inventor: Sa V. Ho, St. Louis, Mo.

[73] Assignee: Monsanto Company, St. Louis, Mo.

[21] Appl. No.: 581,233

[22] Filed: Sep. 12, 1990

[51] Int. Cl.$^5$ .......................... C07K 3/08; C07K 15/04
[52] U.S. Cl. ..................................... 530/399; 530/344; 530/408; 530/409; 530/410; 530/824; 530/825
[58] Field of Search ............... 530/399, 410, 409, 408, 530/825, 344, 824

[56] References Cited

U.S. PATENT DOCUMENTS

| | | | |
|---|---|---|---|
| 4,315,919 | 2/1982 | Shanbrom | 435/71.1 |
| 4,511,502 | 4/1985 | Buider et al. | 260/112 R |
| 4,518,526 | 5/1985 | Olson | 530/399 |
| 4,530,787 | 7/1985 | Shaked et al. | 530/410 |
| 4,652,630 | 3/1987 | Bentle et al. | 530/344 |
| 4,694,073 | 9/1987 | Bentle et al. | 530/399 |
| 4,731,440 | 3/1988 | Bentle et al. | 530/399 |
| 4,766,224 | 8/1988 | Rausch | 530/412 |
| 4,801,691 | 1/1989 | Auer | 530/399 |
| 4,841,023 | 6/1989 | Horowitz | 530/399 X |
| 4,888,416 | 12/1989 | Janski et al. | 530/399 |
| 4,933,434 | 6/1990 | Rudolph et al. | 530/410 |

FOREIGN PATENT DOCUMENTS 8601289 6/1986 World Int. Prop. O. .
8700204 6/1986 World Int. Prop. O. .

OTHER PUBLICATIONS

Biotechnology, 1984; pp. 800–804, Marston et al.

Primary Examiner—Howard E. Schain
Attorney, Agent, or Firm—Wayne R. Eberhardt

[57] ABSTRACT

A method for the solubilization and naturation of somatotropin from refractile bodies produced by r-DNA technology wherein the refractile bodies are dissolved in an aqueous solution comprising a chaotropic agent such as urea or guanidine hydrochloride and a soluble surfactant such as sodium dodecylsulfate. The solubilized protein is exposed to mild oxidation for a time sufficient to allow the protein to form disulfide bonds and refold to its native conformation. The presence of the surfactant suppresses the formation of somatotropin dimers and aggregates and results in higher yields of the desirable monomeric form of the protein.

15 Claims, No Drawings

METHOD OF SOMATOTROPIN NATURATION

FIELD OF INVENTION

This invention relates to the recovery of somatotropin protein produced by recombinant DNA technology, and more particularly, to an improved process for the solubilization and naturation of such proteins.

BACKGROUND OF THE INVENTION

Recombinant DNA technology has permitted the expression of heterologous protein in host cells such as *E. coli* bacteria. In the case of the growth hormone somatotropin, the protein is sequestered in refractile bodies within the cytoplasm of the host cells. The refractile bodies may be recovered from the host cell culture by disrupting the cell so as to release the refractile bodies, and thereupon collecting the refractile bodies as a solid pellet by differential centrifugation. The refractile bodies are solubilized in an aqueous solution of a suitable chaotropic agent such as urea or guanidine hydrochloride at an alkaline pH, generally in the range of 9-12. The solubilized proteins are subsequently naturized by contact with a mild oxidizing agent to form intramolecular disulfide bonds while refolding the protein to its biologically active native conformation. Methods for the solubilization and naturation of somatotropin protein produced by *E. coli* bacteria using recombinant DNA technology are described in U.S. Pat No. 4,511,502 and U.S. Pat. No. 4,652,630, each of which is incorporated herein by reference.

Biologically active somatotropins are effective to enhance animal growth and productivity when administered parenterally as by subcutaneous or intramuscular injection or implantation. Bovine somatotropin for example, is effective to increase milk production of lactating cows, while porcine somatotropin is effective to improve feed efficiency and lean to fat ratio when administered to finishing hogs. The somatotropins may be administered in various liquid or solid formulations for daily or prolonged release applications as well known in the art.

The monomeric form of somatotropin is the most biologically active, and the major yield loss occurring during the solubilization and naturation process is due to the formation of dimer and higher aggregate forms of the protein which are largely removed during further processing and purification of the monomer. Reducing the initial formation of these impurities would not only improve initial monomer yields but also reduce subsequent product losses during the monomer recovery and purification steps.

It is accordingly an object of the present invention to provide an improved process for the solubilization and naturation of somatotropin. It is a further object of the invention to provide an improved process resulting in higher yields of somatotropin monomer during the solubilization and naturation phase of the process. It is a further object of this invention to provide an improved process to reduce the formation of dimer and aggregate forms of somatotropin during the solubilization and naturation thereof. It is a still further object of this invention to improve yields of somatotropin monomer recovered from refractile bodies produced by recombinant DNA technology. These and other objects of the present invention will be apparent from the ensuing description and claims.

SUMMARY

The present invention provides a method for recovering monomeric somatotropin in high yield from refractile bodies obtained through recombinant DNA technology. Briefly stated, the process of the present invention includes the solubilization and naturation of the refractile bodies in an aqueous solution comprising a chaotropic agent such as urea or guanidine hydrochloride and an organic surfactant such as sodium dodecyl sulfate (SDS).

The pH of the solution, usually above 9, and the concentration of the chaotropic agent are selected to effectively achieve solubilization of the somatotropin. The naturation of the solubilized somatotropin is achieved by contacting the solution of solubilized somatotropin with a mild oxidizing agent such as air for a time sufficient to result in the formation of the disulfide bonds present in the native confirmation of the protein and under conditions which permit the somatotropin to "refold" or assume the overall conformational shape of the native protein. Surprisingly, it has been discovered that an organic surfactant present in an amount of from about 0.01 to about 1 g/g protein is effective to inhibit the formation of dimer and aggregate forms of somatotropin during the solubilization and naturation process, resulting in substantial higher yields of the desired monomer. The reduced level of impurities simplifies subsequent monomer purification and recovery with concomitantly higher process yields.

DESCRIPTION OF INVENTION

For purposes of the present invention, the following terms to have the definitions listed below.

The term "somatotropin" is meant to include, but not limited to, mammalian somatotropins such as human, bovine, porcine and ovine somatotropin, and others such as avian somatotropin. Somatotropin produced by recombinant DNA technology in which somatotropin is expressed by genetically transformed bacterial cells may have an amino acid sequence identical to a naturally occurring somatotropin, or may comprise variants in which amino acid residues are either added to, subtracted from or different than the amino acid sequence of the naturally occurring material, provided that such additions, deletions or substitutions in the amino acid sequence do not destroy the bioactivity of the somatotropin. Also included are the somatotropins which are associated with anions or cations, particularly salts or complexes with metal ions. Examples of suitable monovalent metal ions include sodium and potassium while examples of suitable polyvalent metal ions include zinc, iron, calcium, bismuth, barium, magnesium, manganese, aluminum, copper, cobalt, nickel and cadmium. Suitable anions include bicarbonate, acetate, glycine and borate.

"Heterologous" proteins are proteins which are normally not produced by the host cell. Recombinant DNA technology has permitted the expression of relatively large amounts of heterologous proteins such as somatotropin from transformed host cells such as *E. coli*. These proteins are often sequestered in insoluble refractile bodies in the cytoplasm of the host cell.

By "refractile bodies" is meant the inclusion bodies or cytoplasmic aggregates containing, at least in part, the heterologous protein to be recovered. These aggregates appear as bright spots under a phase contrast microscope.

By "host cell" is meant a microbial cell such as bacteria and yeast or other suitable cell including animal and plant cells which has been transformed to express the heterologous protein. Host cells which are contemplated by the present invention are those in which heterologous somatotropin expressed by the cell is sequestered in refractile bodies. An exemplary host cell is *E. coli* K12, strain W3110G [pBGHI], which has been transformed to permit expression of bovine or porcine somatotropin.

"Naturation" refers to the folding and oxidation of the heterologous somatotropin protein to its native conformation to ensure biological activity.

"Folding" refers to the return of the overall conformational shape of the protein to that of the native protein. Folding is accomplished when the amino acid sequence of the protein is free to interact and assume its native secondary and tertiary structure.

"Oxidation" refers to the formation of the intramolecular disulfide bonds in the folded protein to stabilize the native conformation and ensure biological activity.

"Refold Solution" refers to the stock solution obtained as a result of the folding and oxidation in the naturation step.

"Chaotropic Agent" refers to compounds such as guanidine hydrochloride, sodium thiocyanate, urea and various detergents which disrupt the noncovalent intermolecular bonding within the protein, permitting the amino acid chain to assume a random conformational structure.

"Surfactants" refers to surface active compounds which reduce the surface tension of water and include nonionic (e.g., polyethylene oxides), anionic (e.g., sodium dodecyl sulfate) and cationic (e.g., cetylpyridinium chloride) and amphoteric agents.

For purposes of the present invention, refractile bodies can be recovered using standard techniques as described for example in U.S. Pat. No. 4,652,630. For example, the host cell can be disrupted by mechanical means such as a Manton-Gaulin homogenizer or French press. It is preferred that the disruption process be conducted so that cellular debris from the host organism is so disrupted that it fails to sediment from the homogenate solution under low speed centrifugation sufficient to sediment the refractile bodies. The refractile bodies are preferably resuspended, washed and centrifuged again. The supernatant is discarded yielding a substantially pure preparation of refractile bodies. Although not critical to the practice of the present invention, it is preferred that the refractile body preparation be homogenized again to ensure a freely dispersed preparation devoid of agglomerated refractile bodies. The preparation may be homogenized in a Manton-Gaulin homogenizer at 3000-5000 psig.

It is known that somatotropin proteins can be efficiently solubilized from refractile bodies of the host cell by subjecting the refractile bodies to an effective amount and concentration of urea, a weak chaotropic agent, at an alkaline pH. The concentration and absolute amount of urea needed will depend on the pH of the solution and on the amount and kind of somatotropin to be solubilized. Alternatively, the refractile bodies may be solubilized in a strong chaotropic agent such as guanidine hydrochloride. The use of urea is economically favored since it is readily available, relatively inexpensive, ecologically safer than stronger chaotropic agents and does not substantially interfere with the downstream purification procedures.

In the case of the solubilization and naturation process as described in U.S. Pat. No. 4,652,630, the protein related components of a typical refold solution generally consist of from about 30-60% somatotropin monomers, from about 10-30% somatotropin dimer and aggregates and from about 20-50% residues derived from the *E. coli* bacteria, including but not limited to, proteins, membrane fragments, color bodies, endotoxins, pyrogens and nucleic acids. In addition, the refold solution may contain urea at a concentration of from about 1.5 to 6M depending on the type of somatotropin being oxidized. As disclosed in U.S. Pat. No. 4,652,630, a urea concentration of between about 4 and 5M is preferred for naturation of bovine somatotropin, while a concentration of between about 2.5 and 3.5M is preferred for porcine somatotropin.

In the practice of the present invention, the general procedure for solubilization and naturation of somatotropin as described in U.S. Pat. No. 4,652,630 is followed except that an organic surfactant is added to the solution of urea or other chaotropic agent during the solubilization and/or naturation steps. The organic surfactant may be an anionic surfactant such as a carboxylate, sulfonate, sulfate, or phosphate. Sodium dodecyl (lauryl) sulfate is particularly preferred. Nonionic surfactants, particularly the polyoxyethylene or ethoxylate surfactants can also be used. Cationic surfactants such as the aliphatic mono-, di, and polyamines, and amphoteric surfactants such as the imidazolinium derivatives may be useful in some systems. Preferably, the surfactant is incorporated into the solution at the beginning of the solubilization process so that the benefits thereof may be obtained during the entire solubilization and naturation process.

The method of the present invention using urea as the chaotropic agent was demonstrated with several surfactants at different concentrations and with N-alanyl porcine somatotropin (PST) produced by recombinant DNA technology and recovered as an inclusion body suspension following homogenation and centrifugation as described above. All proportions in the following examples are by weight unless otherwise stated.

EXAMPLE 1

100 liters of 3M urea solution were prepared by adding 7.5M urea to chilled water, and the pH adjusted to 11.2-11.4 by the addition of 2.5M NaOH. The temperature of the solution was reduced to 4° C., and 6.0 kg PST refractile body suspension added to provide 10 g/L PST in solution. Sodium dodecylsulfate was added to provide approximately 0.025 weight percent concentration (approximately 0.025 g/g PST). The solution was stirred rapidly but without entraining air for a time sufficient to permit substantially complete oxidation of the PST. Upon completion of the oxidation, the concentration of oxidized monomer in the refold solution relative to total somatotropin was determined by Reverse Phase Chromatography (RPC) to establish refold efficiency. The solution was concentrated to approximately 30 g/L PST with a 30,000 molecular weight cutoff membrane, and diafiltered against 5 volumes of water. The concentrated solution was warmed to room temperature, and the pH adjusted to about 4.9-5.0 with acetic acid to precipitate somatotropin dimers and higher aggregates. Filter aid was added and the solution filtered to remove precipitant. The filtrate was adjusted to about pH 10, concentrated to about 80-90 g/L PST with a membrane, and diafiltered against 10 volumes of 5 mM sodium bicarbonate at pH 10. The resulting concentrate was sterile filtered through a 0.2 micron membrane and freeze dried. Refold efficiency was 70-75%. PST yield on recovery was 85-90% with less than 3% dimer/aggregate content. The concentration of SDS in the final product was about 0.03-0.05 mole SDS per mole of PST (equivalent to 400-700 ppm SDS).

EXAMPLE 2

A series of runs were made to study the effect of various surfactant types and concentrations on PST refold efficiency. PST refractile bodies were solubilized and oxidized in an aqueous solution containing 3M urea at pH 11.0 and 4° C. Total PST concentration was 10 g/L or 6 g/L as indicated in Table I below. After adding the specified surfactant, the solution was stirred and maintained at 4° C. until oxidation was complete, at which point refold efficiency was determined as described in Example 1. The surfactants evaluated and the results obtained were as follows:

| Run No. | PST g/L | Surfactant Type* | g/g PST | Refold Efficiency, % |
|---|---|---|---|---|
| 2.1 | 10 | SDS | 0.02 | 76 |
| 2.2 | 10 | SDS | 0.05 | 64 |
| 2.3 | 10 | SL | 0.10 | 73 |
| 2.4 | 10 | T-80 | 1.0 | 64 |
| 2.5 | 6 | SDS | 0.02 | 70 |
| 2.6 | 10 | control | | 40-45 |

*SDS - sodium dodecyl sulfate
SL - sodium laurate
T-80 - Tween 80 (sorbitan monooleate polyoxyalkylene derivative)

The above Examples illustrate the discovery of the present invention that adding surfactant to an aqueous solution of a chaotropic agent used for solubilization and naturation of porcine somatotropin results in a significant increase in the amount of correctly folded, oxidized monomeric form of the somatotropin.

Additional examples were conducted with N-methionyl and N-alanyl bovine somatotropin under the following conditions of solubilization and refolding:
protein concentration—4 and 10 g/l
surfactant—sodium dodecyl sulfate (SDS)
SDS concentration—0.02 and 0.04 g/g protein
urea concentration—4.5M
temperature—4° C.
pH—11-11.5

Refold efficiency for the bovine somatotropins ranged from about 60 to 80% for the control runs, and from about 50 to 80% in the presence of SDS which generally showed a zero or slightly negative effect at these test conditions. It is known however, that refold efficiency for bovine and other somatotropin decreases as the protein concentration is increased due to increased formation of dimer and aggregate protein. The use of surfactants in accordance with the present invention would be expected to show a positive effect on the naturation of bovine somatotropin at higher protein concentrations such as 15 to 20 g/L or more, thereby making it possible to increase capacity of existing systems without reducing refold efficiency. The use of surfactants to enhance the refold efficiency of bovine somatotropin is accordingly included in the scope of the present invention. Other variations in the general process such as the use of surfactants and chaotropic agents not specifically identified herein, and specific operating conditions will be readily apparent to those skilled in the art and are likewise included herein.

I claim:

1. In a method for the solubilization and naturation of somatotropin protein from refractile bodies of a host cell containing said protein which comprises contacting said bodies with an aqueous solution of a chaotropic agent at a concentration and pH effective to achieve solubilization and thereafter contacting said solubilized protein with a mild oxidizing agent for a time sufficient to accomplish folding and oxidation of said protein, the improvement comprising including in said aqueous solution of said chaotropic agent a soluble surfactant in an amount effective to increase the relative concentration of the folded and oxidized monomeric form of said somatotropin and decrease the relative concentration of dimer and aggregate forms thereof.

2. The method of claim 1 wherein the surfactant is present in an amount of from about 0.01 to about 1.0 grams per gram of somatotropin.

3. The method of claim 1 wherein said surfactant is an anionic surfactant.

4. The method of claim 3 wherein said surfactant is sodium dodecylsulfate or sodium laurate.

5. The method of claim 4 wherein said surfactant is present in an amount of from about 0.02 to 0.10 grams per gram of somatotropin.

6. The method of claim 3 wherein said surfactant is a nonionic or cationic surfactant.

7. The method of claim 6 wherein said surfactant is a polyoxyalkylene derivative.

8. The method of claim 7 wherein said surfactant is present in an amount of about 1.0 grams per gram of somatotropin.

9. The method of claim 1 wherein said somatotropin is porcine.

10. The method of claim 9 wherein said chaotropic agent is urea or guanidine hydrochloride.

11. The method of claim 10 wherein the concentration of said urea is from about 1 to 8M and the pH of said solution is above about 9.

12. The method of claim 10 wherein said surfactant is sodium dodecylsulfate.

13. The method of claim 10 wherein the concentration of said urea is from about 2.5 to 3.5M, and the pH of said solution is above about 11.

14. The method of claim 1 wherein said somatotropin protein is present in said aqueous solution at a concentration of at least about 3 g/L.

15. The method of claim 14 wherein said somatotropin protein is porcine somatotropin and said concentration is from about 3 to 10 g/L.

* * * * *